(12) United States Patent
Costantino

(10) Patent No.: US 6,443,914 B1
(45) Date of Patent: Sep. 3, 2002

(54) APPARATUS AND METHOD FOR PREVENTING AND TREATING CELLULITE

(75) Inventor: Peter Costantino, Armonk, NY (US)

(73) Assignee: Lysonix, Inc., Carpinteria, CA (US)

( * ) Notice: Subject to any disclaimer, the term of this patent is extended or adjusted under 35 U.S.C. 154(b) by 0 days.

(21) Appl. No.: 09/731,642

(22) Filed: Feb. 12, 2001

Related U.S. Application Data

(63) Continuation-in-part of application No. 09/131,487, filed on Aug. 10, 1998, now abandoned.

(51) Int. Cl.[7] ................................................. A61N 7/00
(52) U.S. Cl. ......................................................... 601/2
(58) Field of Search ............................ 601/2–3; 607/96, 607/100, 101; 600/439, 459

(56) References Cited

U.S. PATENT DOCUMENTS 5,755,753 A * 5/1998 Knowlton .................... 607/101

* cited by examiner

*Primary Examiner*—Ruth S. Smith
(74) *Attorney, Agent, or Firm*—Michael G. Petit

(57) ABSTRACT

An apparatus and method for the treatment of cellulite. The connective tissue subjacent to the dermis provides a barrier resisting protrusion of adipose tissue located beneath the dermis. Such connective tissue is generated or strengthened by applying radiation of appropriate frequency to disrupt or otherwise destroy normal cells within or underlying the dermis adjacent to the interface between the dermis and the subcutaneous adipose tissue, or exclusively within the subcutaneous fat or dermis. Following cell destruction, the body's repair mechanism causes a sheet-like fibrous layer to form at the site of cell destruction which is resistant to the protrusion of depot fat underlying the fibrous layer into the dermis. The technique may be useful for other cosmetic procedures which benefit from a contraction or stabilization of the skin or tissue immediately underlying the epidermis, such as facelifts or strengthening of flaccid tissue.

4 Claims, 2 Drawing Sheets

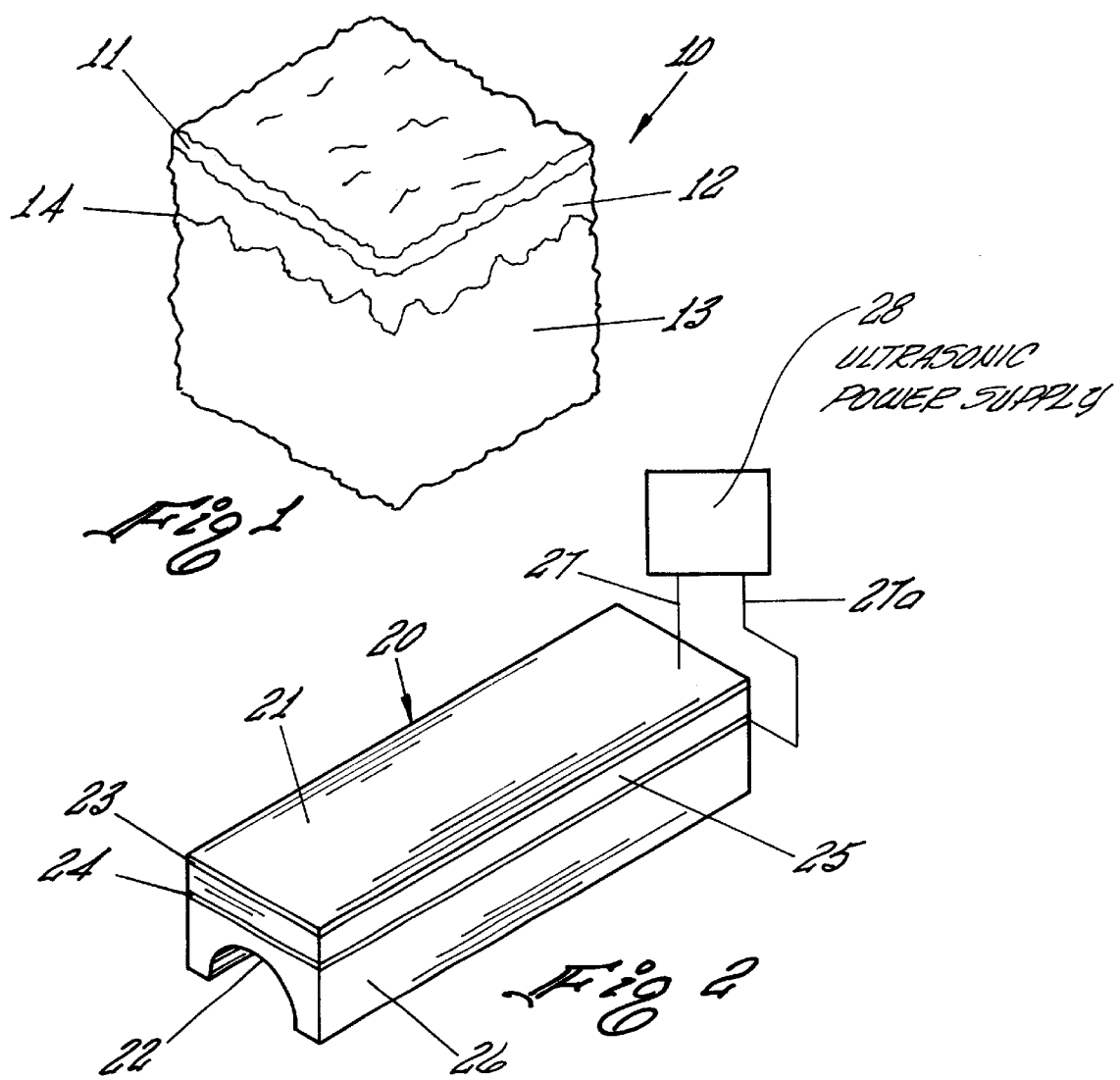
Fig 1
Fig 2
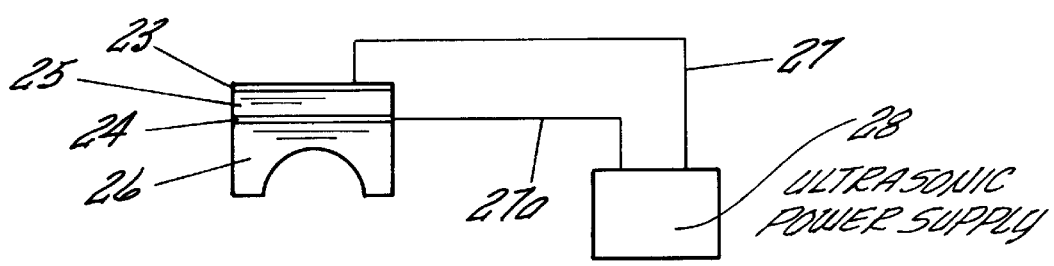
Fig 3

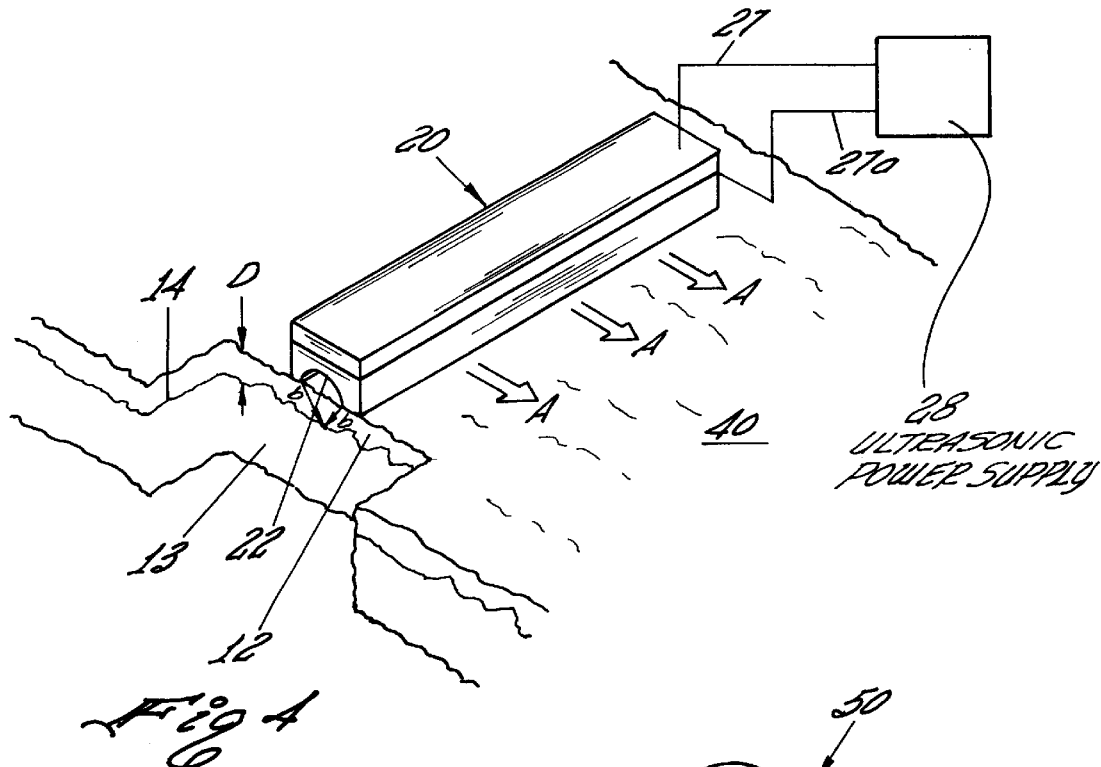
Fig 4
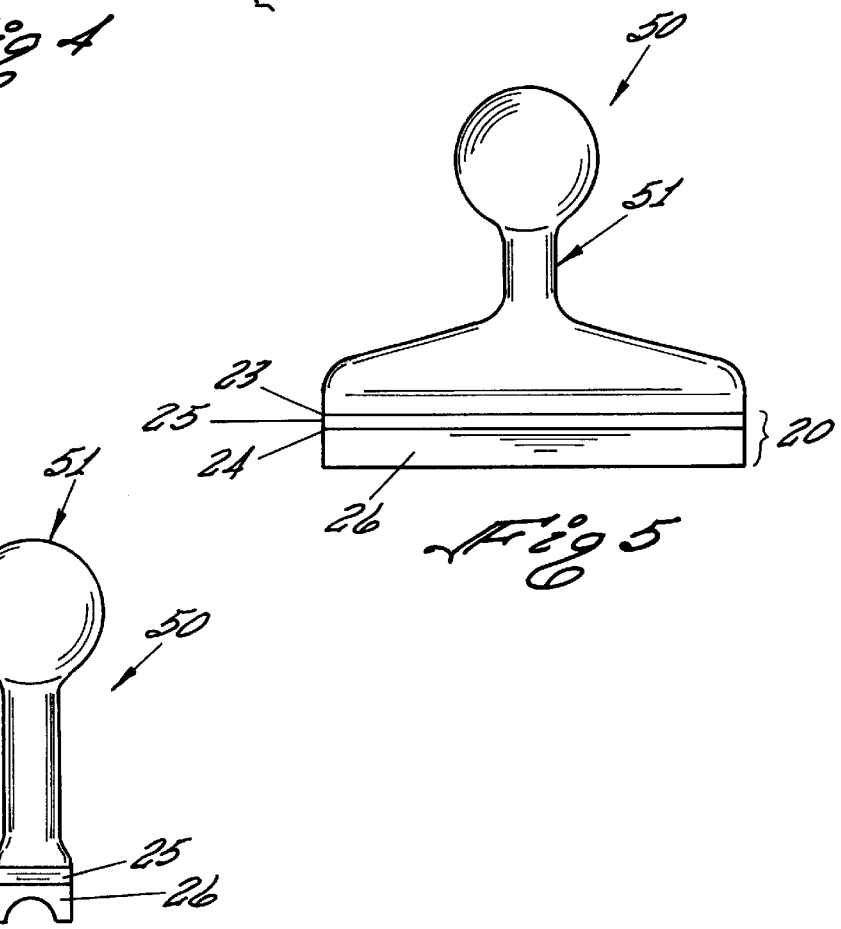
Fig 5
Fig 6

APPARATUS AND METHOD FOR PREVENTING AND TREATING CELLULITE

CROSS REFERENCE TO RELATED APPLICATIONS

This is a continuation-in-part of application Ser. No. 09/131,487; filed Aug. 10, 1998 now abandoned.

BACKGROUND OF THE INVENTION

1. Field of the Invention

This invention relates to an apparatus and method for non-invasively generating a fibrous matrix layer of tissue beneath the skin, and more particularly, preventing subdermal tissue from entering or protruding into to the dermis for treating patients having cellulite, or for the purpose of causing the contraction of laxed or wrinkled tissues below the surface of the epidermis.

2. Prior Art

The distribution of adipose tissue throughout the body is not uniform. In certain portions of the body it is present in great abundance such as in the subcutaneous tissue. A distinction must be made between fat and adipose tissue; the latter being a distinct tissue, the former an oily substance. Adipose tissue consists of small vesicles referred to hereinafter as "fat cells" lodged within the matrix of areolar connective tissue. Fat cells vary greatly in size; having an approximate diameter of about 0.05 mm. They are formed of a delicate protoplasmic membrane filled with the oily substance which is liquid during life but solidifies after death. These fat cells are contained in discrete clusters in the areolae of fine connective tissue.

Areolar tissue is a form of connective tissue wherein the investing connective tissue matrix is separated into areolae or spaces which open into one another and are easily permeated by fluids. Areolar tissue binds different parts of the body together. The elasticity of areolar tissue and the permeability of its areolae allows the various parts of the body to move relative to one another. Most particularly, areolar connective tissue is found beneath the skin in a continuous layer all over the body, connecting the skin (dermis) to subjacent tissues. In many parts the areolae are occupied by fat cells; the matrix and fat cells constituting adipose tissue which is referred to alternatively herein as "depot fat".

It is now well established that the phenomena of cellulite is due to a protrusion of pockets of depot fat from subcutaneous tissue through an elastic layer of connective tissue overlying the depot fat into the dermis. Patients having cellulite appear to exhibit a deficiency in the fibrous layer at the interface between the dermis and the subcutaneous tissue. This deficiency enables depot fat below the interface to protrude up through the fibrous layer and into the dermis thereby causing irregular elevations and depressions of the dermis characterized by a "dimpled" appearance. This condition, and the underlying causes, is discussed by Rosenbaum et al. in Plastic and Reconstructive Surgery, Vol. 104. No. 7, Pages 1934–1939, June, 1998.

Ultrasonic, microwave, nuclear magnetic resonance and other radiative techniques have been employed to provide images of organs within the body and/or to effect treatment of subdermal tissue without necessitating traumatic incision of the overlying tissue. The purpose of such radiative application is directed toward destruction of target cells in a particular target area beneath the skin or to view organs, tumors or other structures for diagnostic purposes. Therapeutic applications include the cauterization of blood vessels via hyperthermia for traumatic injury resulting in bleeding, as occurs, for example, in trauma to the liver. In addition, such radiative treatment may be employed for diagnosing medical conditions, treating prostate hypertrophy, non-invasive lipectomy or for the treatment of brain cancer. Various devices have been designed and disclosed for performing these procedures. Exemplary of such devices is U.S. Pat. No. 5,769,790 to Watkins, et al.; U.S. Pat. No. 5,143,063 to Fellner and U.S. Pat. No. 5,507,790 to Weis. There appears to be no reference in the literature for using radiative energy sources for the purpose of non-invasively forming and/or reinforcing a connective tissue layer beneath the skin of a patient.

Knowlton, in U.S. Pat. No. 5,755,753, discloses a method for tightening skin. The method comprises providing a membrane containing a cooling fluid in combination with a thermal energy source. A reverse thermal gradient is created which cools the surface of the skin while heating underlying collagen-containing layers of tissue. The skin and underlying collagen-containing tissue are then heated without substantially modifying the melanocytes and other epithelial cells in the epidermis. The result is a contraction of collagen tissue and a tightening of the skin. Radiant energy is applied to a variety of different skin layers including the papillary dermis layer, the reticular dermis layer, and even to a subcutaneous layer and to underlying soft tissue. A suitable energy source is one or more RF electrodes. Electrolytic solution contained within the membrane transfers RF energy from the RF electrodes to the underlying collagen tissue. The cooling fluid creates a reverse thermal gradient between the epidermis and the underlying desired layers of about 30 degrees to about 80 degrees C. The creation of the reverse thermal gradient provides for the controlled contraction of collagen tissue, e.g., partial denaturization of the collagen molecules that results in a shrinkage of the collagen tissue, which then extends to a shrinkage of the skin. Creation of the reverse thermal gradient is different from other methods of collagen contraction which typically employ a thermal gradient that has a higher temperature at the surface and decreases with the depth of penetration. Thus, Knowlton's device and method for causing shrinkage of the skin requires cooling the epidermis while heating collagen in the underlying tissue via radiant means such as an RF field.

Knowlton '753 addresses the problem of tightening the skin by increasing cross-linking in collagen in a selected target layer of tissue beneath the skin. That is, the method of Knowlton does not stimulate production of collagen by cells within the target tissue. The method, instead, relies upon increasing the cross linking between amino acids in adjacent collagen fibrils. While Knowlton '753 does not present data specifying a temperature threshold above which the objectives of the method are achieved, the thermoregulating ability of the body renders it difficult, if not impossible, to raise the temperature of a layer of tissue underlying the (cooled) epidermis to a point where denaturation of collagen will occur by employing non-invasive hyperthermia means. The present invention provides a method for stimulating the production of additional collagen in a preselected target area thereby increasing the collagen content in the tissue.

SUMMARY OF THE INVENTION

It is a first object of this invention to provide an apparatus creating controlled tissue injury and repair for structurally reinforcing one or more layers of connective tissue beneath the skin of a patient.

It is another object of this invention to create or reinforce a layer of connective tissue at the interface between the dermis and the subcutaneous tissue of a patient by non-invasive means.

It is yet another object of this invention to provide a method for enhancing the integrity of a connective tissue layer beneath the dermis to prevent lobules comprising adipose tissue from protruding into the layer of skin comprising the dermis.

It is a further object of this invention to provide a means for strengthening the fibrous layer of tissue at the interface between the dermis and the subcutaneous tissue to reduce or prevent cellulite.

The features of the invention believed to be novel are set forth with particularity in the appended claims. However, the invention itself, both as to organization and method of operation together with further objects and advantages thereof may best be understood by reference to the following description taken in conjunction with the accompanying drawings in which:

BRIEF DESCRIPTION OF THE DRAWINGS

FIG. 1 is a schematic cross-sectional view depicting the human epidermis, dermis and subcutaneous tissue.

FIG. 2 is a perspective view of a skin-contacting portion of an ultrasonic vibrator handpiece suitable for the application of ultrasonic energy to tissues at the interface between the dermis and subcutaneous tissue.

FIG. 3 is a end-on view of the skin-contacting portion of the ultrasonic vibrator handpiece of FIG. 2 together with a schematic block diagram of an apparatus for applying radiant or ultrasonic energy to create or reinforce a layer of connective tissue in accordance with the principals of the present invention.

FIG. 4 is a block diagram of an apparatus suitable for applying ultrasonic energy to the interface between the dermis and the subcutaneous tissue of a patient.

FIG. 5 is a front elevational view of a preferred embodiment of the ultrasonic vibrator handpiece of the present invention.

FIG. 6 is a side elevational view of a preferred embodiment of the ultrasonic vibrator handpiece of the present invention.

DESCRIPTION OF THE PREFERRED EMBODIMENTS

The controlled and focused application of traumatic ultrasonic waves to cells comprising a thin layer of tissue adjacent to and including the interface between the dermis and subcutaneous adipose tissue results in tissue destruction followed by an inflammatory response accompanied by the migration of fibroblasts into the area. The similar use of such controlled and focused traumatic energy could be used to create a like tissue response fully within the subcutaneous fat or dermis depending upon the "individualized clinical" condition of the patient under treatment. The intentional directed infiltration of fibroblasts to the thin layer of tissue including the interface may be used to reinforce the structural integrity thereof resulting in an amelioration or elimination of subdermal fat protrusion (cellulite).

Turning now to FIG. 1, a cross section of skin and subdermal tissue of a patient having cellulite is shown generally at 10. The tissue at 10 comprises the epidermis 11, the dermis 12 and subcutaneous adipose tissue 13. The interface 14 between the dermis 12 and subcutaneous adipose tissue 13 is a thin layer of connective tissue which loosely holds the fat cells comprising the adipose tissue 13 in juxtaposition to one another. The fibrous matrix may be viewed much as a fishnet having an elastic capability. Due to the collagen composition of the layer of connective tissue at the interface, the elastic matrix may be more or less irregularly deformable by fat cell aggregations 15 (fat lobules) comprising the underlying subcutaneous adipose tissue. In patients with cellulite, the fibrous layer comprising the interface 14 appears to be less substantial and more deformable than in people who do not present cellulite.

In order to strengthen the fibrous layer comprising the interface 14 to prevent the protrusion therethrough of the fat lobules 15 comprising adipose tissue 13, a means may be employed to damage tissue in the vicinity of the dermis-subcutaneous tissue interface. Upon disruption of cells in the layer comprising the interface 14, the protective bodily systems produce an infusion of cells which, in part, remove the debris and cause some degree of inflammation. The area is reinforced with an additional amount of connective tissue deposition as part of the tissue repair and healing phase. This phase is followed by a period of maturation of the newly deposited connective tissue, thereby resulting in contracture and tightening of the injured tissues and the tissue overlying dermis-epidermis interface. This newly deposited connective tissue matrix may be used to strengthen the natural fibrous layer between the dermis and subcutaneous tissue.

FIG. 2 shows the skin-contacting portion 20 of an ultrasonic vibrator handpiece in perspective view which can focus ultrasonic energy at a layer of tissue beneath the epidermis. The skin-contacting portion 20 generally comprises an elongate member having an upper surface 21 and a concave lower surface 22. Conductive layers 23 and 24 provide electrically conductive means for applying an alternating electric field across a piezoelectric crystal 25 which is in mechanical vibratory communication with a metallic member 26. The electrode 20 receives an alternating voltage through leads 27 and 27a from a ultrasonic power source 28. The electrode 20 is symmetric along its length as shown in FIG. 3.

FIG. 3 is an end-on view of the ultrasonic probe of FIG. 2 showing the curvature of the concave surface. The curvature of the concave surface 22 of the skin-contacting portion of the ultrasonic handpiece is adapted to focus ultrasonic energy applied to the upper skin surface to a line located a distance D below the upper surface of the skin. The distance D is preferably the thickness of the dermis with the region of cell disruption limited to a narrow vertical depth of about 0.5–5 mm but the capable of being focused to a depth extending an additional 2–3 cm below the dermis to achieve the desired result for the treatment of cellulite, depending upon the clinical situation. The ultrasonic energy may be focused within the dermis if such is required for the treatment of laxed or flaccid tissue (dermal-epidermal aytids).

FIG. 4 is a schematic, partially cutaway diagram of the skin 40 showing the layer of tissue comprising the dermis 12, the layer of subcutaneous adipose tissue 13 and the interface 14 between the respective aforesaid layers of tissue. The concave surface 22 of the skin-contacting portion 20 of the ultrasonic vibrator handpiece 50 (see FIGS. 5 and 6) is brought into contact with the surface of the skin 40. The ultrasonic power source 28 applies an alternating electrical voltage to conductive layers 23 and 24 thereby inducing the piezoelectric crystal 25 sandwiched therebetween to mechanically vibrate at an ultrasonic frequency, preferably in the 500 KHZ–1MHZ range. The skin-contacting portion 20 is advanced across the skin in a direction A (shown by the broad arrows 1) thereby covering the area of the skin presenting cellulite. The ultrasonic vibratory waves indicated at the thin arrows ↑ b are focused to have maximum amplitude within a band of tissue which band has a thickness which includes tissue at or near the interface 14 a distance D beneath the skin surface.

In practice, the skin-contacting portion 20 of the ultrasonic vibratory handpiece 50 is attached to a handle portion 51 to facilitate manipulation of the device as shown in FIGS. 5 and 6. The handle portion 51 is adapted to be affixed to the upper surface 21 of the skin-contacting portion 20 and grasped by a hand. FIG. 5 is a front elevational view of the handpiece 50. A side elevational view of the handpiece 50 is shown in FIG. 6.

It may be advantageous to employ a means for mechanically displacing the protruding fat lobules downwards into the main portion of subcutaneous adipose tissue either prior to, during ultrasonic treatment or immediately following treatment. The latter may be accomplished by applying a compression dressing comprising a smooth anatomically conforming plate to the skin area overlying the treated area and applying pressure thereto with an elastic member compressed thereagainst.

The method described hereinabove obviates the need for the intraoperative cooling of the skin during treatment of the target layer of tissue and does not rely on the temperature induced cross linking of extant collagen in order to provide a reinforced layer of tissue.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What I claim is:

1. A method for treating cellulite in an area of skin of a patient by reinforcing a layer of connective tissue which layer includes the interface between the dermis and subcutaneous tissue underlying the area of skin of the patient consisting essentially of the application of focused ultrasonic vibrational energy to tissue comprising said layer in a quantity of energy sufficient to cause damage to normal cells in said layer of tissue comprising the interface.

2. The method of claim 1 wherein said layer of connective tissue has a thickness between 0.5 mm and 5 mm.

3. The method of claim 2 wherein said layer of connective tissue lies in a plane underlying and substantially parallel to the dermis.

4. The method of claim 1 wherein said layer of connective tissue lies in a plane underlying and substantially parallel to the dermis.

* * * * *